US010368731B2

(12) United States Patent
Wortelboer

(10) Patent No.: US 10,368,731 B2
(45) Date of Patent: Aug. 6, 2019

(54) RADIAL IMAGING SYSTEM AND METHOD

(71) Applicant: KONINKLIJKE PHILIPS N.V., Eindhoven (NL)

(72) Inventor: Pippinus Maarten Robertus Wortelboer, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/737,355

(22) PCT Filed: Jun. 7, 2016

(86) PCT No.: PCT/EP2016/062920
§ 371 (c)(1),
(2) Date: Dec. 18, 2017

(87) PCT Pub. No.: WO2016/202647
PCT Pub. Date: Dec. 22, 2016

(65) Prior Publication Data
US 2018/0160892 A1    Jun. 14, 2018

(30) Foreign Application Priority Data
Jun. 19, 2015 (EP) .................................... 15172886

(51) Int. Cl.
*A61B 1/267* (2006.01)
*A61B 1/05* (2006.01)
(Continued)

(52) U.S. Cl.
CPC ............ *A61B 1/267* (2013.01); *A61B 1/05* (2013.01); *A61B 1/0615* (2013.01);
(Continued)

(58) Field of Classification Search
None
See application file for complete search history.

(56) References Cited

U.S. PATENT DOCUMENTS 5,004,339 A * 4/1991 Pryor ..................... G01B 11/00
250/559.39
7,110,124 B2 * 9/2006 Jensen .................. A61B 1/227
356/626
(Continued)

FOREIGN PATENT DOCUMENTS

WO    2000041615 A1    7/2000
WO      02091913 A1   11/2002
WO    2011143269 A1   11/2011

OTHER PUBLICATIONS

Dorffel et al., "A New Bronchoscopic Method to Measure Airway Size," European Respiratory Journal 14.4, 1999, pp. 783-788. (Year: 1999).*

(Continued)

*Primary Examiner* — Christopher Braniff

(57) ABSTRACT

A radial imaging system is provided for capturing an image of an object which extends radially around an image sensor in an object plane. A reflector (42) is used for reflecting incident light (46) to a generally axial direction. The image sensor (40) receives the generally axially directed reflected light, and it has a stepped reflector surface having a series of reflecting linear facets (48) which together form a generally curved, e.g. concave surface. This design enables improved uniformity of the imaging performance with respect to the radial distance to the object being imaged.

17 Claims, 13 Drawing Sheets

(51) Int. Cl.
  *A61B 1/06* (2006.01)
  *H04N 5/225* (2006.01)
  *A61B 5/107* (2006.01)
  *G03B 37/00* (2006.01)
  *G03B 17/17* (2006.01)
  *A61B 5/00* (2006.01)

(52) U.S. Cl.
  CPC .......... *A61B 1/0676* (2013.01); *A61B 5/1076* (2013.01); *A61B 5/1079* (2013.01); *A61B 5/4818* (2013.01); *G03B 17/17* (2013.01); *G03B 37/005* (2013.01); *H04N 5/2256* (2013.01); *H04N 2005/2255* (2013.01)

(56) References Cited

U.S. PATENT DOCUMENTS

| | | |
|---|---|---|
| 2002/0039186 A1 | 4/2002 | Rosenberg |
| 2007/0038123 A1 | 2/2007 | Fulghum |
| 2007/0270717 A1 | 11/2007 | Tang et al. |
| 2012/0190923 A1 | 7/2012 | Kunz et al. |
| 2014/0378845 A1 | 12/2014 | Nadkarni |

OTHER PUBLICATIONS

Dörffel, W. et al., "A new bronchoscopic method to measure airway size", European Respiratory Journal, Jan. 1, 1999, pp. 783-788.

Hoffstein, V., "The acoustic reflection technique for non-invasive assessment of upper airway area", European Respiratory Journal, 4.5, 1991, pp. 601-611.

\* cited by examiner

RADIAL IMAGING SYSTEM AND METHOD

FIELD OF THE INVENTION

The invention relates to a radial imaging system.

CROSS-REFERENCE TO PRIOR APPLICATIONS

This application is the U.S. National Phase application under 35 U.S.C. § 371 of International Application Ser. No. PCT/EP2016/062920, filed on 7 Jun. 2016, which claims the benefit of European Application No. 15172886.2, filed on 19 Jun. 2015. These applications are hereby incorporated by reference herein.

BACKGROUND OF THE INVENTION

An example of a radial imaging system comprises a reflecting cone which redirects light received (basically) radially inwardly to a (basically) axial direction, for collection by an axially aligned camera.

One use of such an arrangement is part of a catheter camera, in which the cross section of a passageway in which the catheter is located is to be inspected. An example of the use of such a catheter camera is for analysis of the upper airway, for determining the causes of obstructive sleep apnea.

Obstructive sleep apnea (OSA) is the most common kind of sleep apnea, affecting up to one in eighteen people, and is characterized by the occurrence of pauses in breathing, or instances of shallow or infrequent breathing, during sleep. It is caused by blockage or obstruction of the oral cavity or upper airway, often due to loss of muscular tone induced by the onset of old age, or (temporary) by abuse of drugs or alcohol.

A range of therapies exist for treatment of OSA, the most common of which is positive airway pressure (PAP), in which a ventilator is used to deliver a stream of air through the airway at a controlled pressure, in order to hold open the airway. PAP is needed in more severe cases, where patients exhibit an apnea hypopnea index (AHI)>30. OSA patients may also suffer from daytime sleepiness and require therapy to prevent the development of comorbidities over the longer term. Mild-moderate OSA patients often have more difficulty adhering to PAP therapy because the disease burden is not as strong as in severe patients, and are therefore reluctant to submit to so invasive a therapy. In these cases, various alternative treatments exist, such as positional therapy, mandibular advancement (oral appliances), upper airway surgery and implantable devices.

In each of these therapies, however, it is important to understand which part(s) of the upper airway in particular is (are) causing obstruction, such that the therapy can be directed most effectively. This explains the interest in dynamic examinations of the upper airway preferably in a non-invasive way. One approach is to perform an examination of the airway non-invasively using acoustic reflectometry techniques. In such techniques, acoustic waves are propagated along the airway of the patient, by an emitter, via the mouth or nose, and reflections are listened for using a microphone adjacent to the emitter. It is possible, through algorithmic analysis of the detected reflections (see for example: Hoffstein, V., and J. J. Fredberg. "The acoustic reflection technique for non-invasive assessment of upper airway area." European Respiratory Journal 4.5 (1991): 602-611.), to determine an estimate of the cross-sectional area of the examined airway as a function of distance from the emitter. From this, narrowing of the airway at particular locations can be identified, and the specific positions therefore of airway obstructions ascertained.

Reflectometry techniques however suffer the disadvantage that the accuracy of cross-sectional area estimations declines with distance from the emitter. This is compounded by acoustic leakage and also patient movements during the measurement process, which both act to further compromise the accuracy of the obtained results. Furthermore, since the first obstruction encountered by a wave propagating along the airway causes reflection of much of the wave's initial intensity, reflections from subsequent portions of the airway are typically too weak in intensity to derive any accurate measurements. Hence it is typically only possible to accurately determine the location of the upper-most airway obstruction using these techniques.

It is known instead to use endoscopic procedures, in particular procedures for inspecting or investigating the patency of the human upper airway. Using a standard flexible endoscope for airway examination, specific sites in the upper airway can be inspected for some time to see whether temporary obstructions occur. This however requires the endoscope to be moved from one spot to the other during an examination which is time-consuming and inconvenient for the patient. For this reason endoscopic examination during natural sleep did not become part of common practice. An alternative version which has acquired some acceptation in current practice involves bringing the patient to artificial sleep by means of sedative drugs. This is believed to cause collapses at sites that also participate in real sleep apneas and hypopneas. Also the sedation relieves the discomfort of endoscope travel.

To inspect the upper airway at some discrete critical sites, it is also possible to use a catheter with multiple image sensors; once the catheter has been inserted it can remain in the same position during a longer period without additional discomfort for the patient. The interpretation of the images acquired at multiple sites over a long period is very time consuming.

Image sensors can also be used to obtain a measure of radial distance, for example if a ring is illuminated around the inside of the airway, the captured image sensor information in respect of the ring image can be analyzed to derive distance information, and thereby enable the shape of the internal airway passage to be derived.

For example, an endoscope may have a light generating means capable of producing an outwardly directed ring (or radial plane) of light, such that when inserted into a tube-like airway, cross sectional contours of the airway may be illuminated for inspection by a camera.

One known means of providing such a light pattern is to direct collimated laser light from an optical fiber toward a deflecting cone whose angle is such as to deflect the incident light radially, for example at 90 degrees, from its surface in all directions around it. The effect is to create a 'ring' pattern of light projecting outwards from the cone, which may then be used to illuminate a circumferential section of an airway. In particular, there are two variations of this concept. In a first, the cone has a reflective outer surface, and is arranged with its tip facing in the direction of the oncoming light, such that light is reflected directly out from its surface. In a second, the cone is arranged with its base facing toward the oncoming light and the pitch arranged such that light incident from the optical fiber on the internal walls of the cone is reflected by total internal reflection in the direction of the opposing wall, through which it is transmitted, deflecting due to refraction as it does so into a path which is at 90 degrees to the initial incident light.

The reflected light is then captured by a camera. This may be achieved by positioning the camera with the inner wall being examined within the field of view, or else another reflecting cone may be used to redirect the reflected light back to an almost axial direction for capture by an axially aligned camera.

It is possible to create multiple ring patterns of light, at a series of spaced points along the airway. This can for example be achieved by means of providing multiple illumination units along the catheter, each with its own laser, optical fiber (optionally a GRIN lens) and cone.

This invention relates in particular to the reflector used to redirect the received incident radial light towards a camera (or any type of image sensor). A standard reflecting cone may be used, with a circular base and a tip (apex) which lies on the normal line through the center of the circle. The lateral surface of the cone is formed by straight line segments joining the apex to the perimeter of the base. This circular cone reflector is fully characterized by the distance of the tip to the base and the angle ($\mu$) the straight lines connecting the perimeter to the tip make with the base plane. The angle at the tip is given by $\pi-2\mu$.

The tip angle and the distance to the camera are chosen such that the camera captures all projected rings with a radius in a very specific range.

This arrangement has a problem that the sensitivity to changes in the radius of the rings depends strongly on the ring radius itself: the farther away the ring being imaged, the less sensitive. The reflecting cone arrangement is therefore not able to be effective over a large range of possible distances from the central axis to the wall of the duct under examination and it prevents uniform measurement accuracy.

Desired therefore is a simple optical arrangement which addresses these problems.

SUMMARY OF THE INVENTION

The invention is defined by the claims.

According to an aspect of the invention, there is provided a radial imaging system for capturing an image of an object which extends around an image sensor in an object plane, the system comprising:

a reflector for reflecting incident generally radial light to a generally axial direction; and an image sensor for receiving the generally axially directed reflected light, wherein the reflector comprises a stepped reflector surface having a series of reflecting linear facets in sequence between a radial innermost portion and a radial outermost portion of the reflector, the linear facets together forming a generally curved surface, wherein each facet is for reflecting incident generally radial light from a different range of radial distances to the image sensor.

Note that by a "linear" facet is meant that in cross section in a plane which includes the axis (around which the radial imaging takes place), the facet is a straight line.

In 3 dimensions, the reflector for example defines a faceted cone. The term "cone" is used in a general way in the description below to include such a structure. It may for example be axisymmetric and thus enable a 360 degree side-view when combined with a single forward looking image sensor. In 3 dimensions, each facet is thus a section of a regular cone surface (and is not a planar surface), and the different facets are at different angles, i.e. they are sections of a regular cone with a different apex angle.

References in the claims and description below to the "center" of a facet refer to the center point within the cross section, i.e. half way along the line which defines the facet when viewed in cross section. When extended to 3 dimensions, a center point of a facet becomes equivalent to a circle of points around the middle of the facet.

By "generally curved surface" is meant that if the center (in 2 dimensions) of each facet is connected by a smooth line, it will be a curve not a straight line. Preferably, it is a generally concave surface. In 3 dimensions, the general shape is then a concave solid of rotation.

The arrangement improves the total light capturing as compared to a conventional straight (i.e. regular) cone (which is equivalent to a single facet), and also is better able to preserve the shape (when the sensed image is presented on a display) of any closed curve in a plane perpendicular to the image sensor and reflector cone.

From the polar radius around the polar angle of the contour in the sensed image, the real radius of the captured shape can be calculated. The shape may be a closed shape, or else it may a portion of a closed shape, or it may a series of discontinuous sections which, if joined together, define such as closed shape.

Object (light) points close to the cone may be reflected into the image sensor to a less extent than points farther away. This means an image sensor with high sensitivity can be used without having the risk of blooming (glow) in the image sensor image from light points close to the reflector cone. Furthermore there is redundancy as several paths co-exist to transmit the light of an object point to the image sensor which makes the sensor distance detection less sensitive to particles between light point, reflector cone and image sensor.

If the image sensor and reflector cone are contained in a transparent envelope, external contamination is not likely to completely block the distance measurement.

The generally axial directed reflected light is directed from the reflector surface to the input to the image sensor. For the purposes of explanation, this may for example be treated as a single imaging point on the axis. For example it may function as a pin-hole light input. An input lens may be provided to the image sensor. This will change the path analysis slightly and the rays will not then converge to a point, but will be focused by the lens.

For a set of light paths which extend between the center of each facet (in 2D cross section, as defined above) and input to the image sensor (and these light paths may for example be characterized by integer multiples of a fixed (camera) view angle) the light directions incident to the facet center (from the objected being imaged) may be parallel. This provides a first design run for designing the reflector surface, and it gives rise to the general concave shape.

For the set of light paths, there may be a linear relationship between the angle of incidence to the imaging point and a radial distance to the intersection of the light path with the object plane. This object point is basically the source of the incident light—at the radial distanced which is to be measured. This arrangement means that the resolution of the measurement of radial distance is more uniform over distance, in that the incident angle detected by the image sensor is linearly related to the radial distance of the object.

For the set of light paths, there may instead be a linear relationship between a radial position on a captured image corresponding to an incident light path and a radial distance to the intersection of the light path with the object plane. This arrangement again means that the resolution of the measurement of radial distance is more uniform over distance, in that the radial position in the image sensor output image is linearly related to the radial distance of the object.

The reflector may comprise connection sections between the reflecting linear facets, wherein the connection sections are:

parallel to the said light directions incident to the facet centers; or at a mid-way angle between the light paths from the facet centers on each side towards the imaging point.

These conditions make sure the connection sections do not block incident light from reaching the facets, and do not block reflected light from the facet reaching the imaging point.

There may be between 2 and 200 facets (inclusive). For example, there may be less than 150, or less than 100, or less than 80, or less than 60 or less than 40, or less than 20 facets. There may be 2 or more, or 3 or more, or 5 or more facets. The upper limit is for example determined by the accuracy with which the reflector can be made, and the wavelength of the light used. Each facet has finite width, and a continuum of rays in one cone-shaped sector can all reach the image sensor. An arbitrary object point will always be reflected in at least one facet and from the angle by which it reaches the input to the image sensor (together with the angle of the facet) the radial distance can be determined. The same relation can be used as holds for a single straight cone. Thus, the standard way of calculating distance may be used. The width of the ring in the image sensor associated with a functional facet with its center at a specific cone radius is smaller with increasing number of facets, and the resolution is limited by the number of pixels in this smallest ring.

The invention also provides a catheter for use in determining the presence and location of obstructions in an upper airway, the catheter comprising:

at least one radial imaging system as defined above, wherein the image sensor is aligned along or parallel to the catheter axis; and a light source for generating illumination light and directing it radially outwardly within the object plane.

The catheter may comprise a plurality of radial imaging systems arranged such that, upon insertion in an upper airway, they are aligned to coincide with one or more of the soft palate (velum), the oropharynx, the tongue base and the epiglottis.

Examples in accordance with another aspect of the invention provide a radial imaging method for capturing an image of an object which extends around an image sensor in an object plane, the method comprising:

reflecting incident generally radial light to a generally axial direction; and receiving the generally axially directed reflected light at an image sensor, wherein the reflector comprises a stepped reflector surface having a series of reflecting linear facets in sequence between a radial innermost portion and a radial outermost portion of the reflector, the linear facets together forming a generally curved surface, each reflecting linear facet generates an image of a range of radial distances to the object plane.

This method makes use of the reflector design outlined above.

The received image may be interpreted to determine the radial distance to the object.

In one example, the interpreting comprises:

allocating different portions of the received image to different reflecting linear facets; and based on the set of portions in which a particular point is imaged, determining a possible range of radial distances.

This is a logic-based approach for finding the object distance, by considering which facets "see" the object.

In another example, the interpreting comprises:

overlaying the captured image with a polar grid that has bands which relates to the inner and outer edges of all of the linear facets, thereby defining a set of bands in which each band corresponds to a single facet; and calculating the object point radius from the polar radius in the image by processing each band separately.

Associated with each image band within the polar grid is a band of object points; these bands may overlap.

This approach is based on treating each facet as a portion of a conventional regular cone, and processing the image accordingly.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a radial imaging system for capturing an image of an object which extends radially around an image sensor in an object plane. A reflector is used for reflecting incident generally radial light to a generally axial direction. The image sensor receives the generally axially directed reflected light, and it has a stepped reflector surface having a series of reflecting linear facets which together form a generally curved, e.g. concave surface. This design enables improved uniformity of the imaging performance with respect to the radial distance to the object being imaged.

The invention may for example be used for imaging with a conduit. This may have non-medical applications for imaging non-living objects such as pipes, channels and tunnels as well as for medical imaging applications such as for imaging airway passages, intestinal passageway or capillaries or arteries. The imaging system may for example be integrated into a catheter.

Figure 1:
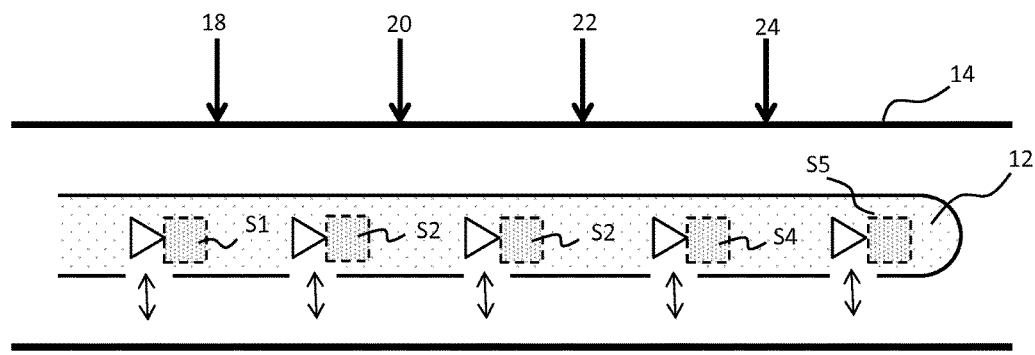
FIG. 1 shows a schematic illustration of a length section of an example catheter disposed inside an airway.

By way of illustration, FIG. 1 schematically depicts an example catheter 12 according to one or more embodiments of the invention, arranged within a stretch of an upper airway 14. Along the length of the airway are indicated four anatomical regions or features, labeled 18, 20, 22, and 24, these, by way of non-limiting example, representing the soft palate (velum), the oropharynx, the tongue base and the epiglottis respectively. Disposed within the airway 14 is a catheter 12, which comprises a series of optical sensors S1 to S5. They each comprise a laser light source for generating light generally axially, a reflector for redirecting the light to include at least a component in the radial direction, a reflector for redirecting reflected light from the side wall of the duct being investigated towards an image sensor for capturing an image of side wall of the duct being investigated. The image shows the radial distance to the duct 14. Instead of redirecting the reflected light by a second cone towards the image sensor field of view, the laser light may be generated in a radial outward direction rather than axially, so that there is only a single cone for capturing the light and directing it to the image sensor.

The optical arrangement is represented schematically in FIG. 1 as a single triangle.

Figure 2:
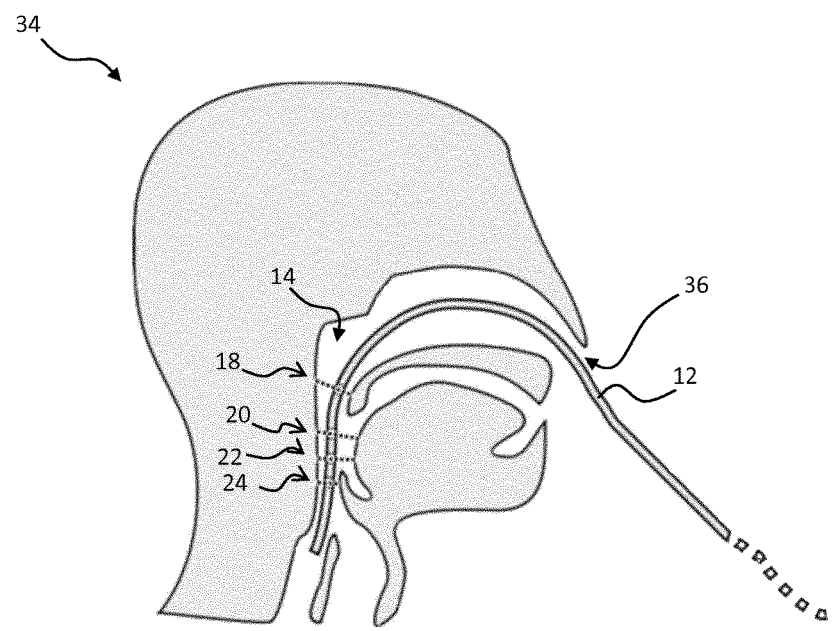
FIG. 2 shows a schematic illustration of an example catheter inserted into a patient's nasal cavity and upper airway.

For illustration, FIG. 2 schematically shows the catheter 12 disposed in the upper airway of a patient 34, having been inserted via the nose 36 of the patient. The approximate positions of the four anatomical regions of FIG. 1 (velum 18, oropharynx 20, tongue base 22, and epiglottis 24) are indicated along the airway 14 of the patient 34.

As mentioned above, the use of a regular circular cone for reflecting the incident reflected radial light to the image sensor field of view has a problem that the sensitivity to changes in the radius of the rings depends strongly on the ring radius itself: the farther away the ring the less sensitive. This invention relates specifically to the reflecting cone for redirecting the inward radial light (which has been reflected from the duct) towards the image sensor.

Figure 3:
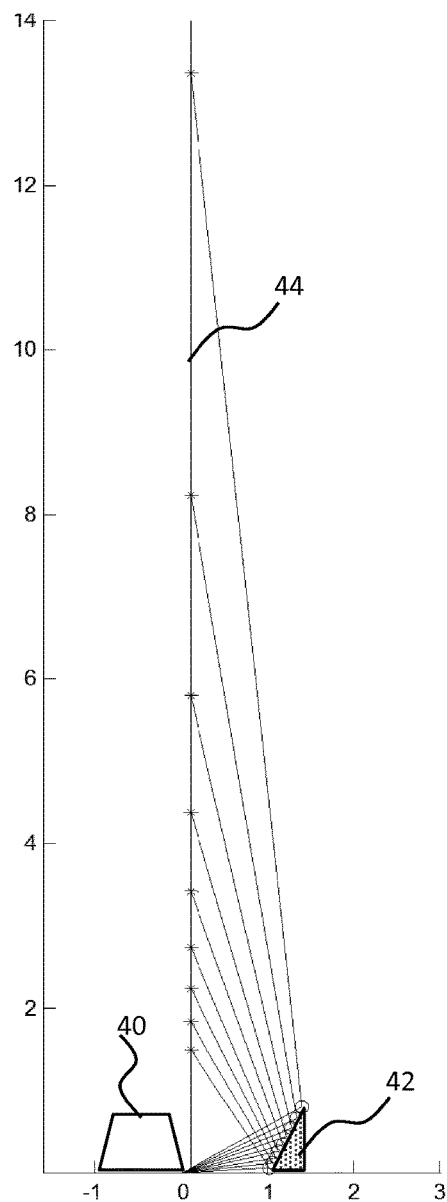
FIGS. 3 and 4 are used to show a problem that the sensitivity to changes in the radius of the object depends strongly on the radius itself.
Figure 4:
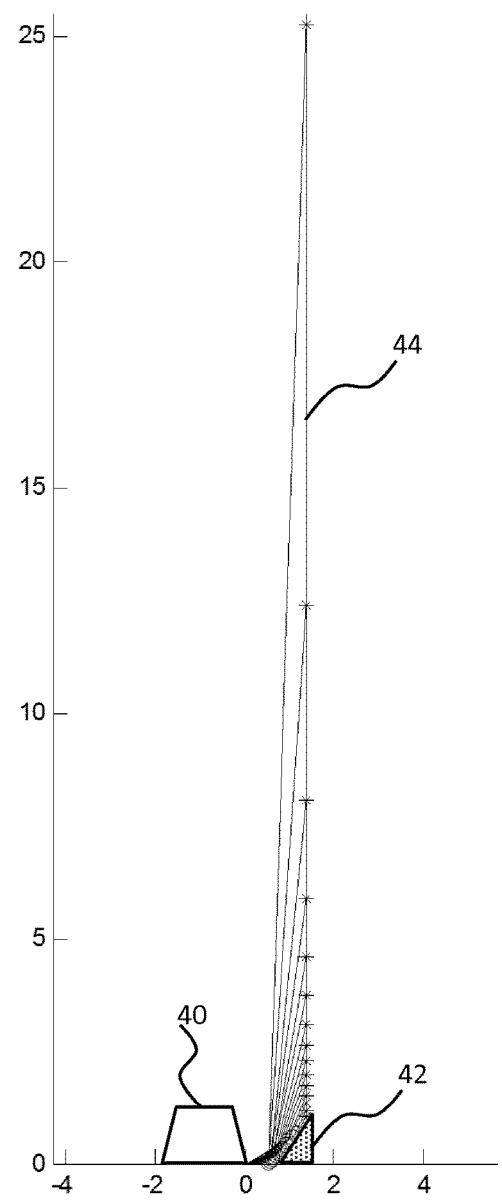

This problem is illustrated in FIGS. 3 and 4. Each shows the top half cross section with the image sensor 40 at the left and a reflecting cone 42 at the right. Specific rays which originate from a vertical laser plane 44 are shown that enter the image sensor at an angle that is a multiple of a fixed angle step. This vertical plane can be considered to be an object plane, in that the distance to the nearest object point within this plane is what is imaged by the image sensor. This fixed angle step represents an incremental change in the field of the view of the image sensor. The object points are marked by the stars along the laser plane 44.

In FIG. 3, the laser plane 44 is in front of the image sensor cone while in FIG. 4 the laser plane 44 is behind the image sensor cone 42. In both cases, the density of points is rather large at a close distance and reduces strongly with the distance from the sensor. In FIG. 3 the ring closest to the sensor is captured as a small ring in the image sensor, while in the FIG. 4 this ring maps into a large ring in the captured image.

The invention provides a design of multi-faceted cone. The position of each facet and the angle of its surface are derived from two parameters: 1) the radial distance of the laser point (or more generally the 'object point') that is to be reflected into the image sensor, and 2) the required angle of incidence in the image sensor of this reflected object point. Thus, each facet is for receiving light from a particular range of radial distances from the central axis of the catheter, and reflecting this light towards the image sensor. As far as the image sensor is concerned, each facet is at a different part of the field of view of the image sensor. Thus, each facet maps received light from a particular range of radial distances to a particular part of the field of view of the image sensor.

The approach of the invention is applicable to measuring the radial distance (in a single step) of any contour that appears in a plane perpendicular to the image sensor and cone axes. The term 'object point' is used to denote a point of this contour within the "object plane". Moreover multiple contours can be measured simultaneously as long as their line type (color, width, dash type) can be recognized in the image sensor. The discussion below focuses on a single contour, but the approach applies in principle to any number of contours.

Figure 5:
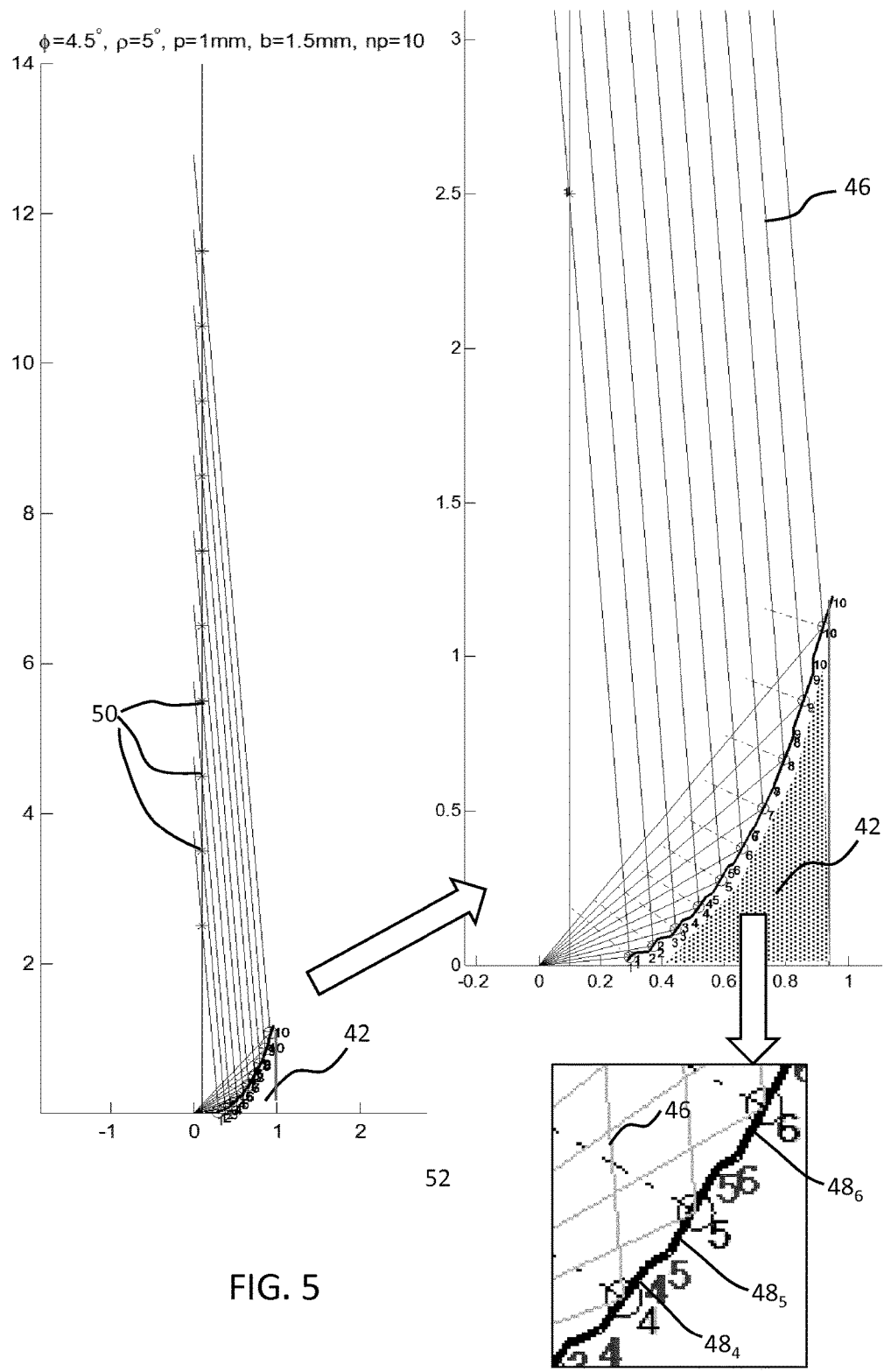
FIG. 5 shows an example of a reflector design.

FIG. 5 shows an example of a resulting design. It shows a cross section in the plane including the rotation axis, i.e. a radial plane. The image sensor is aimed at enabling the distance to the axis to be measured, i.e. the radius contour of the duct being imaged. The reflecting cone 42 has multiple facets. The cone is globally curved, for example concave, and piecewise linear. Thus, in cross section, the shape is not a straight line (as for a regular cone) or a smooth concave curve (as for a parabolic reflector for example) but is a set of connected straight line portions.

The number of these straight line portion corresponds to the number of facets, which may be any number from 2 or from 3 or from 5 up to a maximum. This maximum may be 200, 150, 100, 80, 60, 40 or 20 for example.

The design is such that there is a series of equidistant object points 50 captured in the image sensor at an angle that is linearly indexed. Thus, a given distance along the radial outward direction between object points is translated by the reflector to a given angular increment to the center of the field of view of the image sensor.

The incident rays 46 all originate at equally spaced object points and those rays which lead to the center of the facets (these are the lines shown) are also all parallel. The facet center is the middle of the line in the cross section shown. These rays 46 thus hit the center of the facets which can be seen in the enlarged portion 52. Three of the facets $48_4$, $48_5$ and $48_6$ are shown. The position and angle of each facet (marked by a dashed normal direction) is such that the central ray is reflected into the center of the image sensor field of view (i.e. a camera pin-hole) under an angle that is a multiple of 5 degrees in this example. The parallel incoming rays all make an angle of 4.5 degrees with the vertical.

Note that if the centers of the facets are joined to form a smooth curve (in the cross sectional plane as defined above), the normal to the curve at each facet center is different to the normal direction to the facet itself. Thus, there is a stepped shape as shown.

Note that the assumption that all rays are directed to a single point at the image sensor input is for explanation only. There may be a lens or other optical system which changes the light paths. However, the light paths from the facet centers are for example stepped by a constant angular increment.

The facets from a sequence between a radial innermost portion and a radial outermost portion of the reflector. Thus, the facets are arranged in a sequence in a cross section including the axis (from which distance is to be measured) rather than in a sequence circumferentially around the axis.

The function of the reflector is thus to redirect light received generally radially inwardly towards a generally axial direction towards the input of the image sensor.

The facets are connected together by connecting portions in the form of non-functional intermediate facets. This can also be seen in the enlarged portion 52.

The functional facets 4, 5, and 6 are the planar portions which receive the incident ray as drawn in the figure. The intermediate non-functional facets are the steps between these planar portions. Only the principal rays in the center of the functional facets are plotted and it can be verified that the normal direction changes slightly. The further away the facet is from the centerline (the axis of symmetry) the steeper the slope in order to provide reflection towards the center of the image sensor field of view.

In one example of the faceted cone explained below, the radial distance of an object point is proportional to the angle of incidence to the image sensor (pin-hole).

Figure 6:
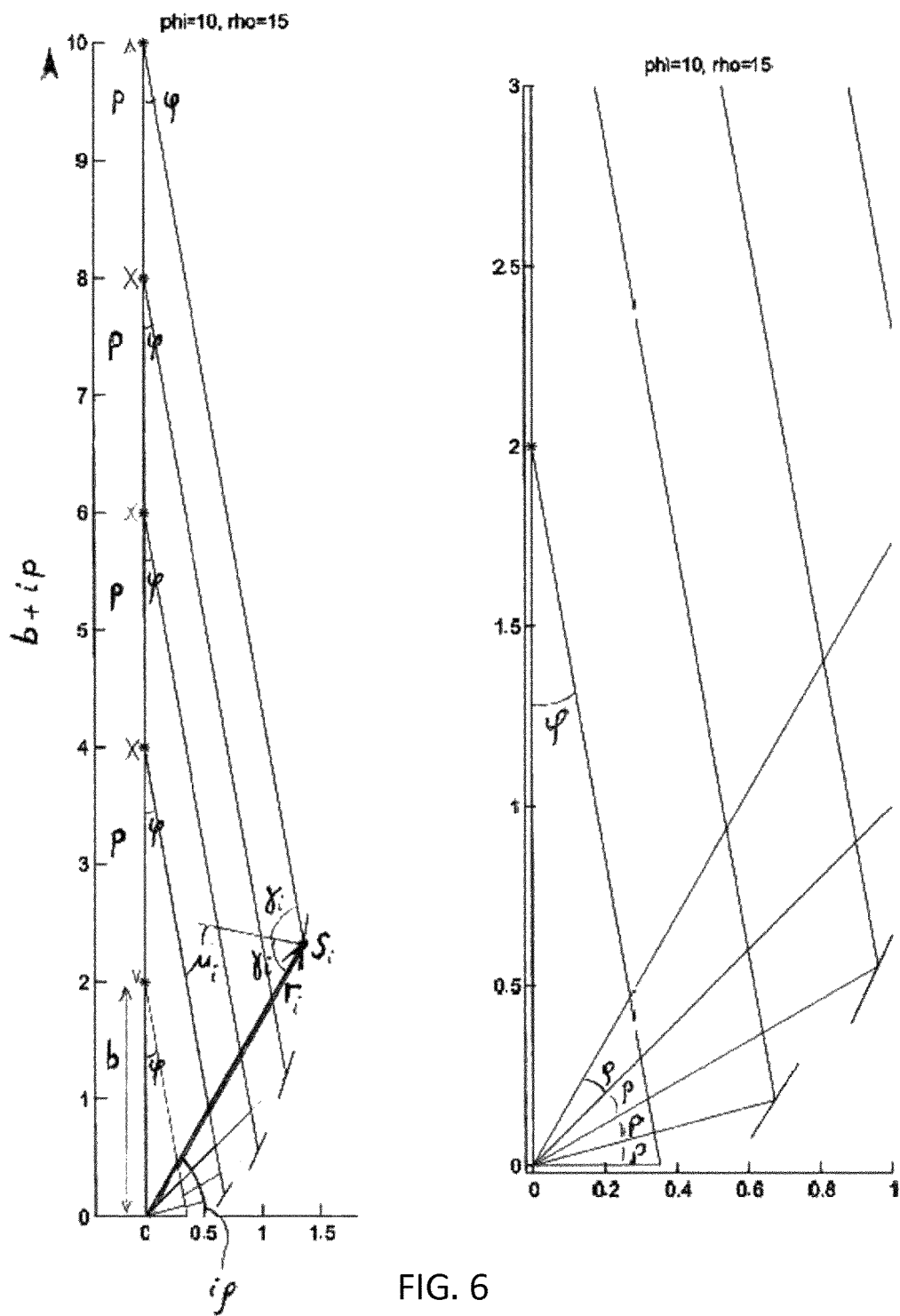
FIG. 6 shows the derivation of the facet position and orientation for object points in the plane of the image sensor input.

FIG. 6 shows the derivation of the facet position and orientation for object points in the plane of the image sensor pin-hole.

The image sensor pin-hole is in the origin.

Let:

$$w_{iy} = b_0 + (i-1)p$$

be the series of points on the y-axis ($i=1, 2, \ldots n_p$). So starting from $b_0$ there is a constant pitch p.

All incoming rays are parallel and have the same angle $\varphi$ with the vertical. Thus, for a set of light paths which extend between the center of each facet and the imaging point, the light directions incident to the facet center (the "incoming rays") are parallel. The angle of incidence step in the image sensor is $\rho$. Thus each $\rho$ degree angle section incident to the image sensor corresponds to a pitch band p in the radial direction in the plane of inspection. Thus, for the set of light paths (the ones which meet the facet centers), there is a linear relationship between the angle of incidence to the imaging point and a radial distance to the intersection of the light path with the object plane.

Before explaining how the position and orientation of all the facets can be derived and how these facets are best merged into a continuous faceted cone, it is noted that the object points could equally be defined in a plane at a distance d from the origin. As the rays are all parallel the pitch does not change; only the first point b changes. Given this value of b it is possible to calculate $b_0$:

$$b_0 = b + \frac{d}{\tan\varphi} \quad (1)$$

Using the sine rule the following relationships are derived:

$$r_i = \frac{\sin\varphi}{\sin 2\gamma_i}(b_0 + (i-1)p) \quad (2)$$

$$\gamma_i = \frac{1}{4}\pi - \frac{1}{2}\varphi + \frac{1}{2}i\rho$$

$$\mu_i = \frac{1}{4}\pi - \frac{1}{2}\varphi - \frac{1}{2}i\rho$$

The index i is the counter of the points along the object plane (the vertical line) that can for instance represent an intersection with a passageway being inspected, such as an airway wall.

The coordinates of the reflection facet center are:

$$(r_{ix}, r_{iy}) = \frac{\sin\varphi}{\cos(\varphi - i\rho)}(b_0 + (i-1)p)(\cos i\rho, \sin i\rho) \quad (3)$$

By substituting Equation (1) in Equation (3):

$$(r_{ix}, r_{iy}) = \frac{\sin\varphi(b + (i-1)p) + d\cos\varphi}{\cos(\varphi - i\rho)}(\cos i\rho, \sin i\rho) \quad (4)$$

Thus Equation (4) gives the coordinates of the facet center as a function of the index i for a given set of parameters b, d, p, $\varphi$, and $\rho$. The orientation of each facet is defined by Equation (2).

The width of the facets still needs to be derived. The width of all individual facets (reflection rings) can be chosen such that:

1) reflected rays from a facet can all reach the image sensor without obstruction; and 2) parallel rays directed towards a facet can all reach the facet without obstruction.

Figure 7:
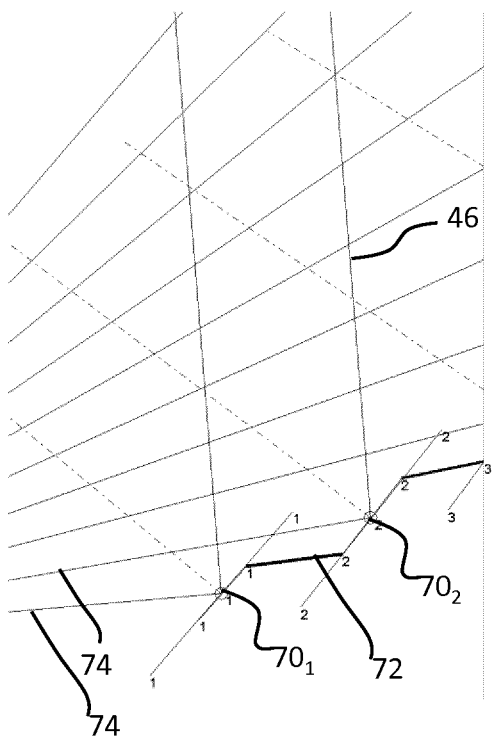
FIG. 7 shows the width and angle of facets closest to the central axis.

FIG. 7 shows that the width of facets closest to the central axis (facets 1 and 2) is limited; they only extend halfway to the neighboring facets. The dividing line is right in the middle making an angle ½$\rho$ with both rays from the center points 70$_1$ and 70$_2$. Thus, the non-functional intermediate facet 72, which may be considered to be a connection section, lies in a direction which bisects the two rays 74 which are directed to the image sensor. Thus, the intermediate facets (connection sections) are at a mid-way angle between the light paths of the facets on each side towards the imaging point. These facets ensure that all reflected rays reach the image sensor—the non-functional intermediate facets 72 do not get in the way.

Figure 8:
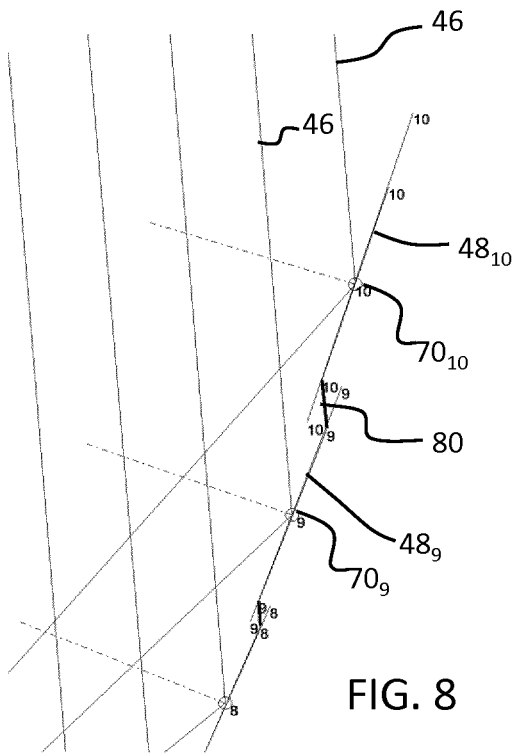
FIG. 8 shows the width and angle of facets furthest from the central axis.

FIG. 8 shows that the width of facets furthest from the central axis (facets 9 and 10) is also limited such that facets points never extend beyond the midline between two parallel rays running to the facet centers. In this case, the non-functional intermediate facets (connection sections) 80 lie in a direction which is parallel and midway between two of the incident beams 46. Thus, the intermediate facets are parallel to the light directions incident to the facet centers.

In this way, all incident parallel beams reach the facet, because they rays are not blocked by the non-functional intermediate facets 80.

Figure 9:
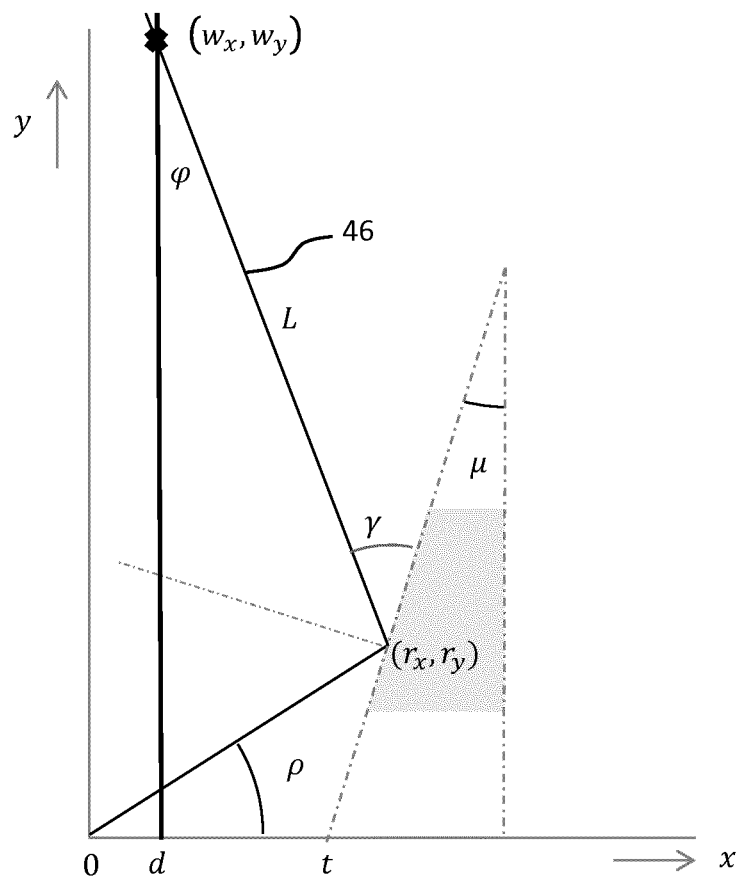
FIG. 9 shows the parameters relevant to the facet design.

For each facet the radial distance calculation from the radial distance in the image sensor image is different, but the general formula behind it is the same. The parameters are given in FIG. 9.

Let $\mu$ be the angle of the normal of the facet reflective side with respect to the horizontal (x) axis, and let t be the distance from the image sensor pin-hole to the tip of the virtually extended cone of the facet of concern. The distance of the object plane to the image sensor pin-hole is d.

The single reflected ray 46 shown makes angle φ with the vertical (incoming part) and angle ρ with the horizontal (reflected part). The relationship between radial distance $w_y$ and angle ρ for a specific facet (defined by μ and t) is derived below.

From tan $$\mu = \frac{r_x - t}{r_y},$$

and tan $$\rho = \frac{r_y}{r_x},$$

the coordinates of the reflection point can be solved:

$$(r_x, r_y) = \frac{t}{1 - \tan\mu \tan\rho}(1, \tan\rho) \quad (5)$$

Furthermore the ray dependent angles can be derived:

$$\gamma = \frac{\pi}{2} - \rho - \mu \quad (6)$$
$$\varphi = \frac{\pi}{2} - \rho - 2\mu$$

The origin of each object point ($w_x$, $w_y$) can be calculated by going back from point ($r_x$, $r_y$) in the direction given by φ over an axial distance of $r_x$–d. The distance (denoted L) between points r and w is $$L = \frac{r_x - d}{\sin\varphi}$$

So:

$$(w_x, w_y) = \quad (7)$$
$$(r_x, r_y) - L(\sin\varphi, -\cos\varphi) = \left(d, \frac{t}{1 - \tan\mu\tan\rho}\left(\tan\rho + \frac{1}{\tan\varphi}\right) - \frac{d}{\tan\varphi}\right)$$

Note that t and μ are different for each facet. Angle ρ is to be determined from the position of the image point; φ then follows from (6).

Figure 10:
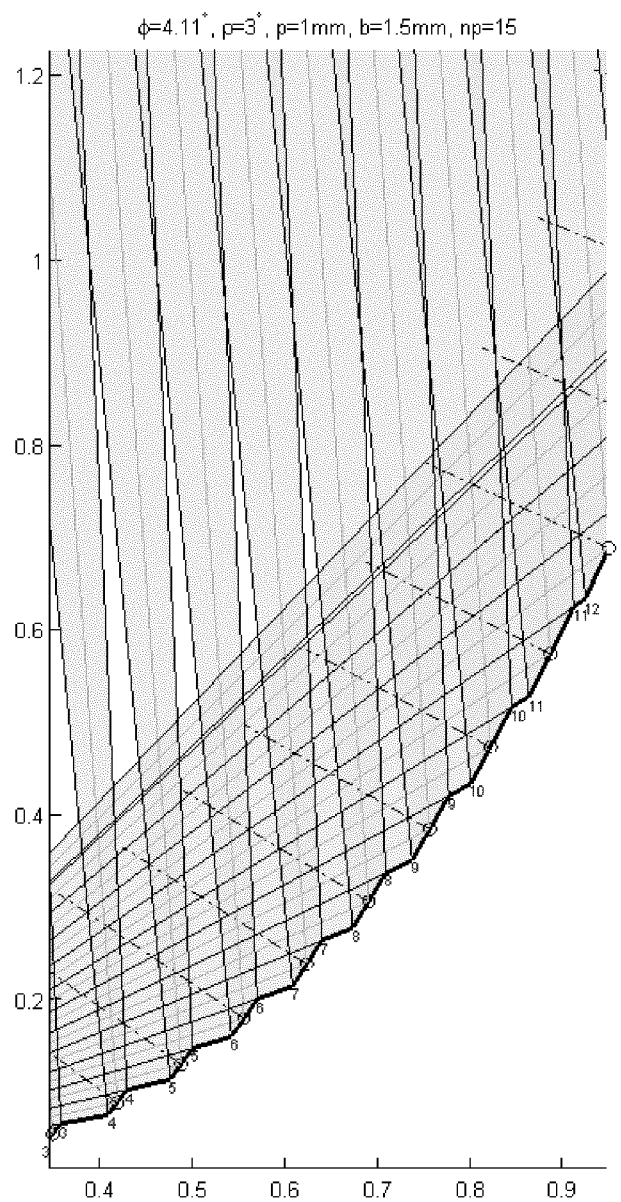
FIG. 10 shows how ranges of object points in the measurement plane generally overlap.

Each facet captures a specific range of object points in the measurement plane. These ranges generally overlap as is illustrated in FIG. 10. This means that all object points are imaged by at least one facet at the image sensor pin-hole. Thus, while the incident rays to the center of each facet are parallel, the rays to the edges of the facets diverge away from the facet, so that the each facet images a larger portion of the object plane 44.

If an object point at a certain radial distance is mapped to the image sensor pin-hole by more than one facet (i.e. where the incident ray bundles overlap) it will appear multiple times in the image sensor image.

This effect is illustrated by simulating the image of a pin-hole image sensor that looks at 5 different rings via a cone with 15 facets. The rings have radii $R_i$:

$R_1$=1.5
$R_2$=4
$R_3$=8
$R_4$=12
$R_5$=16

Note that apart from the i=1 ring, the others are multiples of 4, i.e. evenly spaced radial distances.

Figure 11:
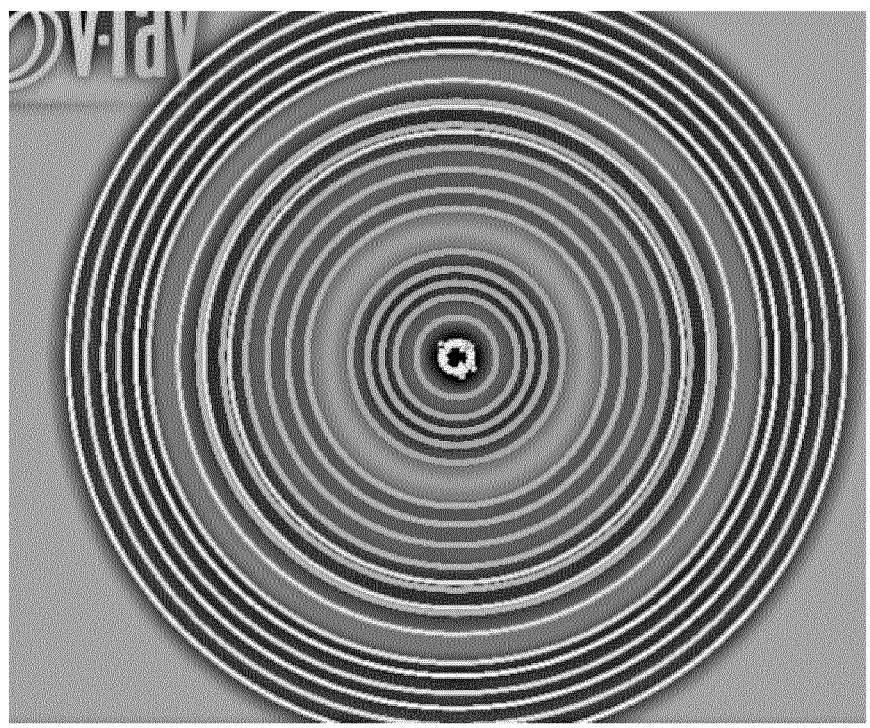
FIG. 11 shows a simulation of the sensed image based on a reflector cone with 15 facets.

The image sensor image for a specific cone design with 15 facets is shown in FIG. 11. The axial distance from the image sensor pin-hole to the plane with the rings is 0.1, and the distance from the axis to the tip of the cone is 0.207.

Although there are only five rings being imaged, there are many more rings seen in the image sensor image. The largest ring (i=5) is imaged 3 times but these three circles are not the outer three circles. They are interleaved with circles for i=4 (note that this has been determined by using a color image sensor view, where each object is illuminated by (or modeled by) a different color light). The i=4 ring is imaged 6 times. The outer rings are interleaved with the i=5 rings as mentioned above, and the inner rings are interleaved with the outermost i=3 rings, of which there are 6. There are 5 i=2 rings but not interleaved, and a bundle of i=1 rings very near the center of the image. There is clearly a lot of overlap and spread.

Figure 12:
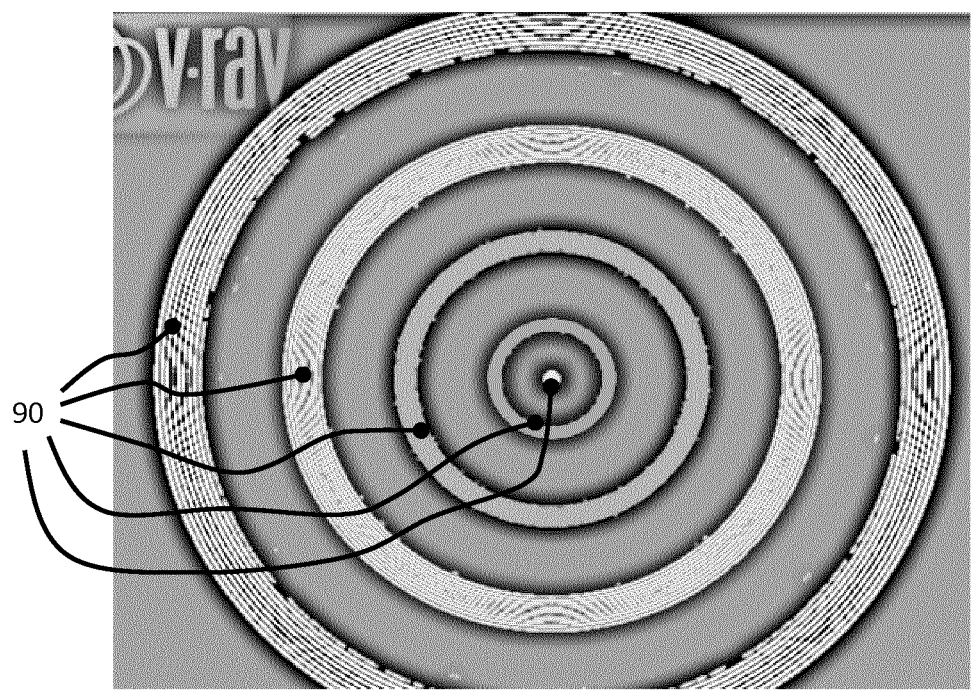
FIG. 12 shows a simulation of the sensed image based on a reflector cone with 100 facets.

By increasing the number of facets to 100, while keeping all other parameters the same, the result is shown in FIG. 12. The number of reflections per ring increases but the distance between these reflections decreases with the number of facets. The rings are now tightly clustered into non-overlapping bands 90.

The width of the bands increases with the ring index i, and the average radius of each bands reproduces the radius of the corresponding original ring. Thus there is the desired linear mapping between the radial distance of the object being imaged, and the angle of incidence to the image sensor pin-hole, as represented on the image by the radial distance from the center of the image.

Figure 13:
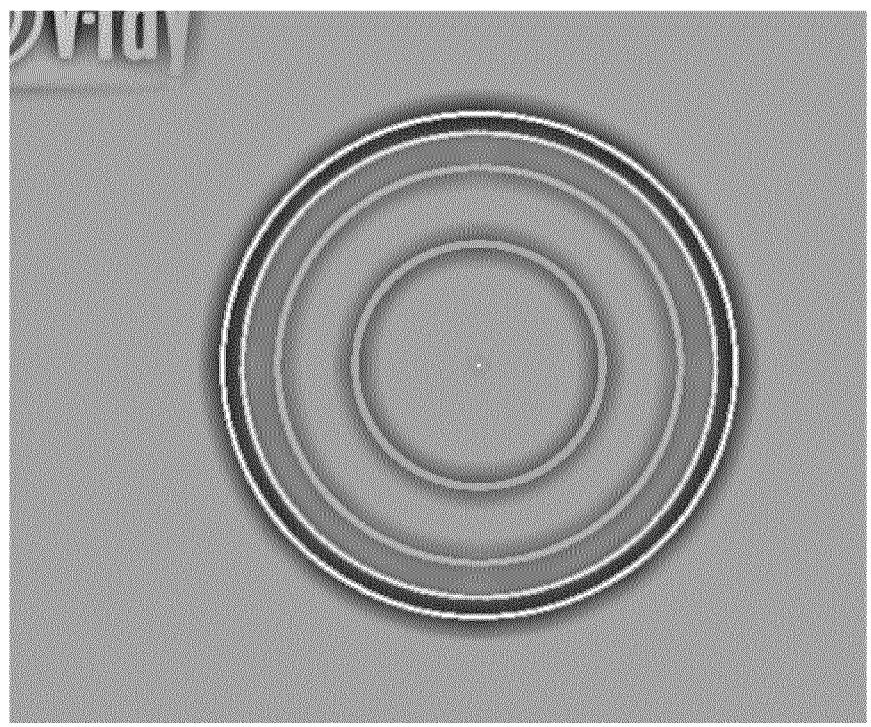
FIG. 13 shows a simulation of the sensed image based on a straight reflector cone.

In FIG. 13 is shown a comparable result for a straight cone with maximum radius R=1.2, base-to-tip height H=0.593, and tip angle 127.4° (μ=26.3°); the tip is at t=1.41 from the pin-hole, and the rings are at d=0.254 from the pin-hole.

The important observation is that the rings in the image have very different distances and thus do not replicate the even radial spacing of the original objects. A further conclusion is that the total amount of reflected light for a straight cone is limited, while for the faceted cone a multiplication is achieved.

In the above analysis multiple object rings were active at the same time. This can be representative in applications in which the shape of multiple 2D contours in a plane close to the image sensor have to be determined. It is also possible to have contours in different parallel planes, but then different conversion formulas have to be applied. The contours may be made identifiable within the image by line color, width, and/or dash type.

In the envisioned catheter application there is only one contour lit per sensor in a specific cross section.

Figure 14:
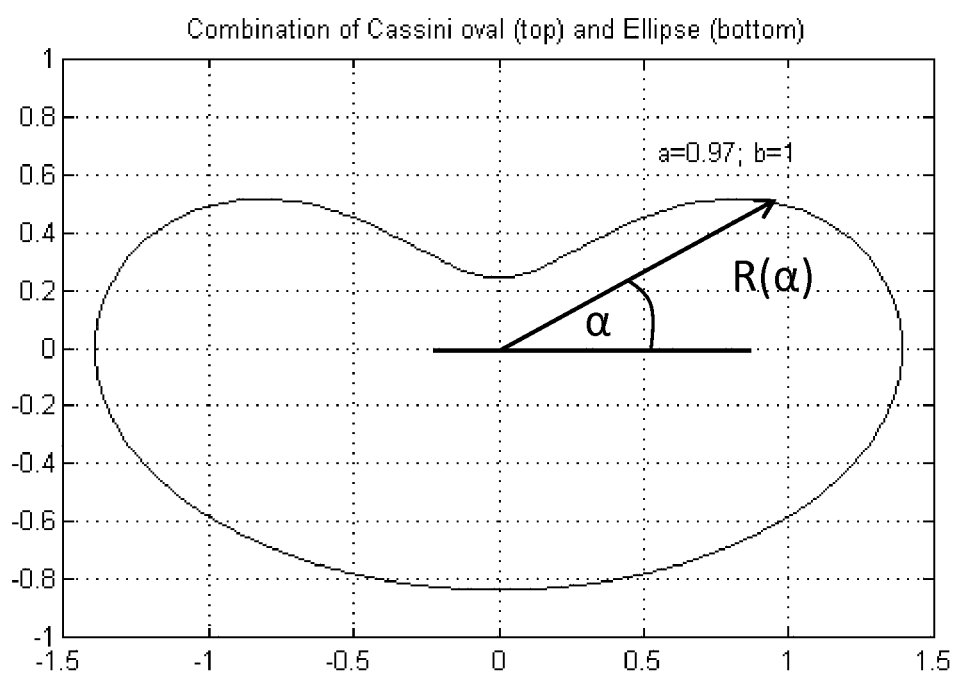
FIG. 14 shows a cross section contour with a variable polar radius.

In general the distance of the sensor center to a contour point is a function of the polar angle (α) associated with the contour point. A characteristic cross section contour is given in FIG. 14 which shows a cross section with a variable polar radius R(α).

In order to calculate a radius from a total received image sensor image, the first step is to overlay the image sensor image with a polar grid that relates to the inner and outer edges of all functional facets.

This polar grid defines a set of bands. Each band corresponds to a single facet, which behaves in the same way as a portion of a straight cone. Thus, in each of these polar bands, conventional rules can be applied for calculating the object point radius from the polar radius in the image. For the object points visible in a band the cone shape outside the corresponding facet is of no concern.

In this way, conventional formulae are used to retrieve the radial distance from the imaged point of a normal straight cone.

As an object point may appear in more than one polar grid band (since it may be imaged by two or more facets), there is redundancy. The operation is as if the object is inspected with multiple cones at the same time because the total light captured is a multiple of the light captured by only a single facet straight cone.

The more facets that are used, the thinner the polar grid bands become (since each band corresponds to a facet) and also the smaller the corresponding object point range will be. This means a high resolution image sensor image is needed to calculate the object point radius from any of the bands in which it appears.

Figure 15:
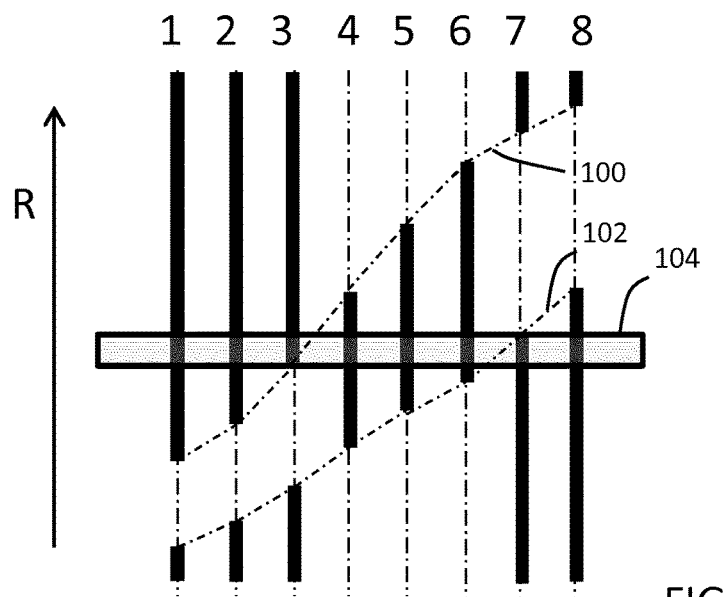
FIG. 15 shows a method for interpreting the sensed image based on a binary account of the object point visibility in different polar grid bands.

There is also an alternative method to determine the object point radius that is purely based on a binary account of the object point visibility in the polar grid bands. This method is explained using FIG. 15.

For each facet (numbered 1 to 8 in this example) there is a band of object point radii r between which an object is imaged. This band is between the lines 100 and 102. In this example, the object point is visible in facets 4, 5 and 6, but not in the other facets. A vertical line is shown for each facet with the bold part indicating a possible object point radius. For facets 4, 5 and 6 the bold part is between the lines 100 and 102 whereas for the other facets it is outside the band 100,102. The intersection of all the possible radii per facet gives the interval of the object point radius. In this example it is easy to conclude that the object point radius lies between the maximum radius of band 3 and the minimum radius of band 7. This interval is indicated by the window 104. This window crosses all the bold bars.

As both the lower and upper limit of the band increase monotonously with the facet index it is only needed to check the facets involved in the visibility switch, so 3 and 4, and 6 and 7.

Let $i_{min}$ and $i_{max}$ be the minimum and maximum index of the facets with a visible object point, and let $\underline{R}(i)$ and $\overline{R}(i)$ be the lower and upper limit of the radius of band i.

The interval can then be found as:

$$<\max(\overline{R}(i_{min}-1),\underline{R}(i_{max}))\ \min(\overline{R}(i_{max}+1),\underline{R}(i_{min}))> \quad (8)$$

The description above explains how to analyze the performance of the multi-facet cone and how to interpret the image sensor image. A discussion of how to design the cone will now be provided.

To build the faceted cone, first a numerical description of the faceted cone surface is needed. To create the surface, the formulae provided above can be implemented in software.

The set of parameters b, d, p, $\varphi$, $\rho$ and $n_p$, can then be adjusted to find a satisfactory design. It is effective to first state the basic requirements and then use the formulae to calculate the remaining parameters.

The inputs for the design are first explained. The image sensor pin-hole is assumed to be in the origin and the image sensor looks to the right (+x direction). The design is axisymmetric and only the radial dimension (+y direction) needs to modeled. The requirements are formulated in terms of the maximum radius of the cone and the range of radial distances that has to be detectable.

Figure 16:
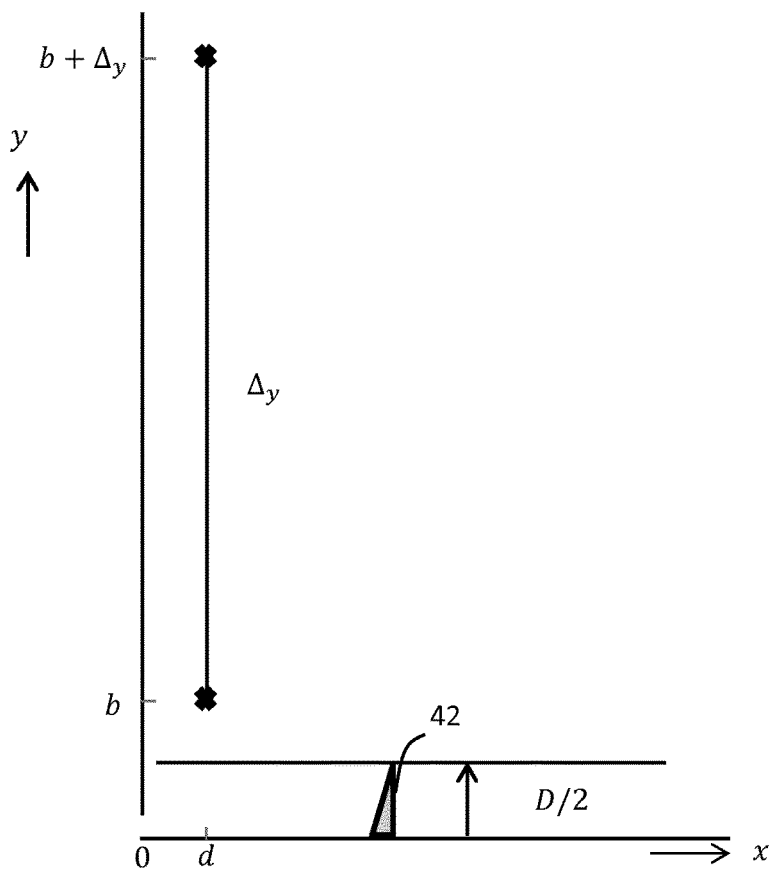
FIG. 16 shows the parameters that define the requirements on size: maximum cone radius (D/2), minimum distance to detect (b), and the size of the detection range ($\Delta_y$)

FIG. 16 shows the parameters that define the requirements on size: maximum cone radius (D/2), minimum distance to detect (b), and the size of the detection range ($\Delta_y$).

Another requirement is that the value $\rho_{max}=n_p\cdot\rho$ should not exceed FOV/2 (FOV=Field of View of the image sensor). $\rho$ is the angle of light incidence to the image sensor pin-hole (see FIG. 9) and $n_p$ is the number of facets. The parameters $\varphi$, t, and d can be solved numerically (or graphically) from the formulas given above. The axial length of the faceted cone follows from the position of the largest facet.

Apart from $n_p$, the number of facets, the global shape of the faceted cone is now determined.

Figure 17:
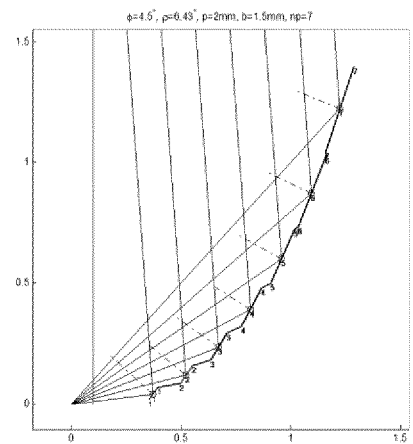
FIGS. 17 to 19 show different reflector cone designs based on different values for the number of facets.
Figure 18:
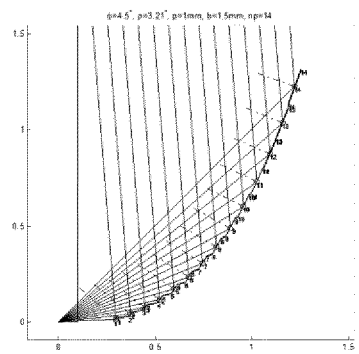
Figure 19:
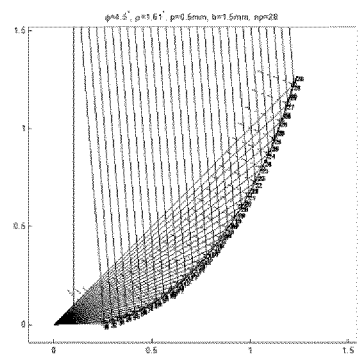

FIGS. 17 to 19 show three different values for $n_p$. These values are 7 (FIG. 17), 14 (FIG. 18) and 28 (FIG. 19). It can be seen that the global shape is the same but smoothness increases with larger $n_p$.

The upper limit of the number of facets can be determined from 1) the accuracy of the manufacturing equipment, and 2) the resolution of the image sensor.

Regarding manufacturing, machining by turning has a limitation by the stability of the tool (chisel) and workpiece on the one hand and the radius of the chisel on the other hand. In principle each facet is turned similar to a normal cone, only at the edges of the functional facets where they meet with the non-functional intermediate facets artifacts may show up. In principle the faceted cone can also be made by replication; a thin reflective coating can be added afterwards.

In the description above, the image sensor angle of incidence step $\rho$ was held constant, but adaptations are possible for instance to correct for the projection after the pin-hole onto the sensor plane. Instead of requiring a constant incidence angle step, a constant radius step in the sensor plane (image plane) may be stipulated. In this case, for the set of light paths (which arrive at the facet centers), there is a linear relationship between a radial position on a captured image corresponding to an incident light path and a radial distance to the intersection of the light path with the object plane.

With this approach a faceted cone can be designed that maps a real contour (in a plane perpendicular to the image sensor optical axis and cone central axis) into a set of similarly shaped curves in the image.

The faceted cone can be used in any application that uses a single forward looking image sensor for measuring the radial distance of detectable markers or lines over the circumference (360 degrees) when the markers and/or lines are all contained in a known plane perpendicular to the cone and image sensor axis. This means that as long as the cone and image sensor assembly can be fixed to a series of parallel planes all perpendicular to the image sensor, then visible contours can be reconstructed in these planes from the image sensor image.

In the example described above, the shape of the faceted cone is globally concave and piecewise linear. The example given is axisymmetric, i.e. rotationally symmetric about the central axis at which the image sensor is located. However, it may not extend completely around the axis. For example, it may be desired to image to one side only of a plane, in which case a half cone is needed. Thus, the imaging system may be for capturing an image of an object which extends only partially and not fully around the image sensor in the object plane. Similarly, the cone may be formed of discontinuous circumferential sections if a continuous ring image is not needed.

One application of particular interest is to improve the performance of an optical catheter sensor for measuring the upper airway patency in OSA patients during natural (or sedated) sleep; in this application a laser plane is created in the sensor module that is perpendicular to the image sensor and cone axis and in the associated cross section in the upper airway a contour lights up. The sensor elements are contained in a capillary.

The problem faced with a normal cone with straight side is that the resolution is unbalanced: for close contour parts the resolution is high and for contour parts at a larger distance the resolution is far less. With the faceted cone, reflectors can be formed that have a more uniform resolution over the distance range of concern. An additional advantage is that object (light) points close to the cone are reflected into the image sensor to a less extent than points farther away; an image sensor with high sensitivity can be used without having the risk of blooming (glow) in the image sensor image (when a contour part is close to or even contacts the image sensor and cone assembly).

Finally the imaging with the faceted cone is less sensitive to contamination on the sensor capillary because there are different paths of an object point (via several facets) to the image sensor.

Another type of application is the inspection of channels that carry a clear internal pattern including cross section contours; any deviation from the designed shape can be detected.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A radial imaging system for capturing an image of an object which extends around an image sensor in an object plane, the system comprising:
    a laser light source for generating illumination light and directing it radially outwardly within the object plane;
    a reflector for reflecting incident generally radial light to a generally axial direction; and
    an image sensor for receiving the generally axially directed reflected light,
    wherein the reflector comprises a stepped reflector surface having a series of reflecting linear facets in sequence between a radial innermost portion and a radial outermost portion of the reflector, the linear facets together forming a generally curved surface, wherein each facet is for reflecting incident generally radial light from a different range of radial distances to the image sensor.

2. A system as claimed in claim 1, wherein the generally axially directed reflected light is directed from the reflector surface to the input to the image sensor.

3. A system as claimed in claim 2, wherein the position and angle of each facet is selected such that for a set of light paths which extend between the center of each facet and the input to the imaging sensor, the light directions incident to the facet center are parallel.

4. A system as claimed in claim 3, wherein the position and angle of each facet is selected such that for the set of light paths, there is a linear relationship between the angle of incidence to the imaging point and a radial distance to the intersection of the light path with the object plane.

5. A system as claimed in claim 3, wherein the position and angle of each facet is selected such that for the set of light paths, there is a linear relationship between a radial position on a captured image corresponding to an incident light path and a radial distance to the intersection of the light path with the object plane.

6. A system as claimed in claim 3, wherein the reflector comprises connection sections between the reflecting linear facets, wherein the connection sections are:
    parallel to the said light directions incident to the facet centers; or
    at a mid-way angle between the light paths of the facets on each side towards the imaging point.

7. A system as claimed in claim 1, wherein there are between 2 and 200 facets.

8. A system as claimed in claim 1, wherein the reflector is axisymmetric.

9. A catheter for use in determining the presence and location of obstructions in an upper airway, the catheter comprising:
    at least one radial imaging system as claimed in claim 1, wherein the image sensor is aligned along or parallel to the catheter axis.

10. A catheter as claimed in claim 9, comprising a plurality of radial imaging systems arranged such that, upon insertion in an upper airway, they are aligned to coincide with one or more of: the velum, the oropharynx, the tongue base and the epiglottis.

11. The system as claimed in claim 1, where there are between 3 and 200 facets.

12. The system as claimed in claim 1, where there are between 5 and 200 facets.

13. A radial imaging method for capturing an image of an object which extends around an image sensor in an object plane, the method comprising:
    reflecting incident generally radial light to a generally axial direction; and
    receiving the generally axially directed reflected light at an image sensor,
    wherein the reflector comprises a stepped reflector surface having a series of reflecting linear facets in sequence between a radial innermost portion and a radial outermost portion of the reflector, the linear facets together forming a generally curved surface, each reflecting linear facet generates an image of a range of radial distances to the object plane.

14. A method as claimed in claim 13, further comprising interpreting the received image to determine the radial distance to the object, wherein the interpreting comprises:
    allocating different portions of the received image to different reflecting linear facets; and
    based on the set of portions in which a particular point is imaged, determining a possible range of radial distances.

15. A method as claimed in claim 13, further comprising interpreting the received image to determine the radial distance to the object, wherein the interpreting comprises:
    overlaying the captured image with a polar grid that has bands which relates to the inner and outer edges of all of the linear facets, thereby defining a set of bands in which each band corresponds to a single facet; and
    calculating the object point radius from the polar radius in the image by processing each band separately.

16. A method as claimed in claim 13, wherein a set of light paths which extend between the center of each facet and an input to the image sensor, there is a linear relationship between the angle of incidence to the image sensor and a radial distance to the intersection of the light path with the object plane.

17. A method as claimed in claim 13, wherein a set of light paths which extend between the center of each facet and an input to the image sensor, there is a linear relationship between the radial position on the captured image corresponding to an incident light path and a radial distance to the intersection of the light path with the object plane.

* * * * *